United States Patent [19]

Gosselin

[11] Patent Number: 5,120,306
[45] Date of Patent: Jun. 9, 1992

[54] DIRECT DELIVERY OF ANTI-INFLAMMATORIES TO THE PROXIMAL SMALL BOWEL

[76] Inventor: Léon F. Gosselin, 587, Place Choquette, Mont St-Hilaire (Quebec), Canada, J3H 3Z6

[21] Appl. No.: 496,667

[22] Filed: Mar. 21, 1990

[51] Int. Cl.$^5$ .................................. A61M 31/00
[52] U.S. Cl. .................... 604/51; 604/264; 604/270
[58] Field of Search ............... 604/264, 270, 48, 49, 604/51, 93; 128/897, 898

[56] References Cited

U.S. PATENT DOCUMENTS

| | | | |
|---|---|---|---|
| 3,922,339 | 11/1975 | Shear | 424/22 |
| 4,190,716 | 2/1980 | Parkinson et al. | 525/334 |
| 4,211,777 | 7/1980 | Chambers | 424/232 |
| 4,298,595 | 11/1981 | Parkinson et al. | 424/78 |
| 4,312,806 | 1/1982 | Lambert et al. | 268/149 |
| 4,440,763 | 4/1984 | Lover | 424/230 |
| 4,496,553 | 1/1985 | Halskov | 514/166 |
| 4,540,685 | 9/1985 | Bauer | 514/162 |
| 4,631,054 | 12/1986 | Kim | 604/270 |
| 4,632,921 | 12/1986 | Bauer | 514/163 |
| 4,657,900 | 4/1987 | Powell et al. | 514/166 |
| 4,663,308 | 5/1987 | Saffran et al. | 514/3 |
| 4,664,256 | 5/1987 | Halskov | 206/213.1 |
| 4,678,807 | 7/1987 | Cotter et al. | 514/552 |
| 4,698,059 | 10/1987 | Johnson | 604/270 |
| 4,753,963 | 6/1988 | Jandacek et al. | 514/552 |
| 4,769,014 | 9/1988 | Russo | 604/270 |

FOREIGN PATENT DOCUMENTS 3151196 6/1983 Fed. Rep. of Germany .
2021409 12/1979 United Kingdom .

OTHER PUBLICATIONS

Enteral Feeding Products—Jul. 1987—Ross Laboratories of Columbus, Ohio, USA (brochure).
Flexiflow Enteral Feeding Tube—Nov. 1985—Ross Laboratories of Columbus, Ohio USA (brochure).
Klotz et al., Drug Research, 35(I), No. 3 (1985) 636-639.

Primary Examiner—C. Fred Rosenbaum
Assistant Examiner—Sharon Finkel
Attorney, Agent, or Firm—Nixon & Vanderhye

[57] ABSTRACT

Transpyloric treatment of small bowel inflammation (e.g. Crohn's disease) by topical application of anti-inflammatory agents such as 5-ASA, 4-ASA or 3-ASA has hitherto been by oral administration of tablets the accurate targeting of which, in the variable environment of the gut, has been impossible. Now, by using an enteric feeding tube, an effective amount of an agent like 5-ASA may be delivered directly to the inflamed segment fo the gastrointestinal tract in patients suffering from inflammatory bowel disease whereby the agent is brough into direct, topical contact with inflamed mucosa while avoiding prior degradation in the stomach.

7 Claims, No Drawings

DIRECT DELIVERY OF ANTI-INFLAMMATORIES TO THE PROXIMAL SMALL BOWEL

BACKGROUND OF THE INVENTION

1. Field of the invention:

This invention relates to a method of delivery of antiinflammatory agents, particularly 5-amino salicyclic acid (5-ASA), 4(4-ASA), and 3-amino salicylic acid (3-ASA) as well as other topically effective therapeutic agents directly to the lower gastrointestinal (G.I.) tract in patients suffering from inflammatory bowel disease. In the above context, the term "lower" means distal to the pyloric sphincter.

2. Description of the prior art

It is well known that inflammatory bowel diseases such as Crohn's disease and ulcerative colitis may be gainfully treated by topical application of 5-ASA (U.S. Pat. No. 4,496,553 and No. 4,540,685). Furthermore, lower G.I. tract ulcers are usefully treated by topical application of steroid preparations.

Access to the inflamed parts is oral or anal. Rectally administered 5-ASA (e.g. via enema in U.S. Pat. No. 4,664,256) enjoys limited systemic absorbtion and consequent good topical effectiveness. However, rectally administered 5-ASA only acts locally on the recto-sigmoidal colon so that more proximal inflammation cannot be treated in this manner. Oral delivery of anti-ulceric steroids and 5-ASA to sites of inflammation located above the transverse colon, and particularly to the proximal small bowel, is more complex and successful delivery with subsequent therapeutic benefit depends on several factors. For instance, gastric emptying time varies from one individual to another and in the same individual may vary according to the size of (orally taken) particles (or tablets) and according to whether the patient is in a fasting or non-fasting state. Furthermore, dwell time in the ileum is also variable and indeed previously surgically treated patients may have a shortened small bowel. Likewise, variations in colonic bacterial flora are possible and indeed certain during antibiotic therapy.

However, the primary difficulty in accurate targeting of orally administered, topically acting steroids and 5-ASA is stomach acidity which destroys such preparations.

In the case of 5-ASA, attempts to overcome this acidity problem have included use of the prodrug sulfasalazine (SAS) which resists stomach acidity to yield free 5-ASA and sulfapyridine via enzymatic cleavage in the large bowel. Unfortunately sulfapyridine gives adverse side effects. Improvements on this principle are disclosed in U.S. Pat. Nos. 4,190,716, 4,298,595 and 4,663,308 although accurate targeting is still limited by the variability of the conditions required for bacterial cleavage.

There exist also enterically coated 5-ASA tablets which protect their contents from stomach acidity and which dissolve gradually to release the active ingredient (hopefully) at the desired site of action. However, variation of gut pH renders it impossible to preselect the final site of action.

Another attempted oral route is the drinking of either a suspension of 5-ASA with simultaneous ingestion of omeprazole which blocks the secretion of hydrochloric acid in the stomach or of a suspension could incorporate extremely small 5-ASA particles made gastric resistant by means of an appropriate coating.

Although the pH of the stomach and possibly that of the duodenum may be modified by the concomitant administration of $H_2$ antagonists or other drugs (like omeprazole), little is known about pH variations in the small and large bowel of patients with inflammatory bowel disease.

As a result it is impossible to predict the exact site of action of any orally taken pH profile-dependent 5-ASA, steroid formulations or other topically active agents since most depend on constant pH profiles not found in the human system.

It is therefore desirable to provide a method of delivering 5-ASA and other topically active agents to an inflamed site in the lower GI tract whereby the active agent is brought into direct, topical contact with inflamed parts of the tract while avoiding prior degradation in the stomach.

To achieve this, the present invention makes use of an enteric feeding tube. Such feeding tubes are in use primarily for providing alimentation to the stomach or to the jejunum via an abdominal incision (see "Enteral Feeding Products"—a brochure dated July 1987 of Ross Laboratories of Columbus, Ohio, U.S.A.). Nasal-/oral use of such tubes for alimentary purposes is also known.

OBJECTS OF THE INVENTION

An object of the present invention is to use an enteric feeding tube for administering a medication to the G.I. tract beyond (viz. distal to) the stomach.

Another object of the invention is to provide a means of accurately targeting the site and rate of delivery of such medications to the desired inflamed areas.

A further object of the invention is to avoid use of prodrugs having adverse side effects.

Another object of the invention is to ensure topical application of anti-inflammatories, such as 5-ASA, at the site of inflammation over an appropriate amount of time (eg 4.0-12.0 hours).

Still another object of the invention is to provide a kit for carrying out the above objects.

A further, more specific object of the invention is to ensure accurate and safe delivery of topically active therapeutic agents such as 5-ASA to the duodenal, jejunal of proximal small bowel and other segments of the lower G.I. tract to allow treatment of severe Crohn's ileitis duodenitis, jejunitis as well as fulminant ulcerative colitis.

SUMMARY OF THE INVENTION

In meeting the above and other objects, the present invention provides a method of delivery of an effective amount of an anti-inflammatory agent, preferably 5-ASA, directly to a target area of the lower gastrointestinal tract in patients suffering from inflammatory bowel disease comprising:

providing a pharmaceutically acceptable suspension containing the agent to be delivered;

providing an enteric tube having first and second ends;

inserting the first end of the enteric tube upstream the target area in the lower gastrointestinal tract distal to the stomach of a patient to be treated; and introducing said solution into the second end of said tube to expel a desired amount of said solution at a desired rate from said first end into the tract.

In this manner, the agent is brought into direct, topical contact with inflamed parts of the lower gastrointestinal tract, while avoiding prior degradation in the stomach.

The invention also provides a kit for delivery of an effective amount of an anti-inflammatory agent, again preferably 5-ASA, directly to the lower gastrointestinal tract in patients suffering from inflammatory bowel disease comprising:

a pharmaceutically acceptable solution containing the agent to be delivered;

a container for said solution; and an enteric tube insertable into the lower gastrointestinal tract distal to the stomach of a patient to be treated.

The invention further provides for the use of an enteric tube for bringing an anti-inflammatory agent into direct, topical contact with inflamed parts of the lower gastrointestinal tract in patients suffering from inflammatory bowel disease, e.g Crohn's disease and ulcerative colitis.

The objects, advantages and other features of the present invention will become more apparent upon reading of the following non-restrictive description of a preferred embodiment thereof.

DETAILED DESCRIPTION OF THE INVENTION

The kind of feeding tube useable according to the invention may be of any medically acceptable constitution. The tube may be made for example of thermoplastic elastomer, silicone rubber or polyurethane although the thermoplastic elastomer is preferred.

The tubes may be used in conjunction with a stylet or bolus of any suitable design for the provision of a solution of anti-inflammatory agent eg 5-ASA solution. Preferably the connector at the top end of the tube is adaptive to syringes and other fluid containers for their direct connection to the tube.

A preferred tube is the Flexiflo ® Enteral Feeding Tube manufactured by Ross Laboratories and disclosed in the company's November 1985 brochure entitled "Enteric Feeding Tube".

Also preferred are the gastronomy kits and jejunal feeding tubes also produced by Ross Laboratories and disclosed in their earlier mentioned July 1987 brochure entitled "Enteral Feeding Products".

Another suitable tube is the so-called Frederick Miller Feeding Tube Set produced by COOK ® of Bloomington, Indiana, U.S.A.

When administering a 5-ASA suspension (using the feeding tube), it is possible either to deliver free 5-ASA to the site of inflammation or to map the pH at sites of inflammation so that an oral suspension containing coated or encapsulated micro-particles having (an) appropriate (pH dependant) release profile(s) can be selected for use after initial treatment with the method or kit according to the invention.

Turning now to the solution of 5-ASA or other topically active therapeutic compounds useable in the present invention, any pharmaceutically acceptable solution or suspension may be used. This would normally be aqueous and a preferred solution is a stable suspension of substantially pure 5-aminosalicylic acid in a saturated, substantially colourless aqueous solution of 5-aminososalicylic acid of pharmaceutical grade purity having a pH of from about 3 to 5 and rendered resistant to colour formation upon storage by the dissolved presence therein, at a concentration of up to about 0.25% w/w, of an amount of bisulfite effective to stabilize the solution against colour formation and degradation eg by oxidation of the 5-aminosalicylic acid by the reaction with any trace amount of oxygen in the solution or in its container.

The way in which this preferred solution may be prepared is disclosed in U.S. patent No. 4,657,900.

The method aspect of the invention is carried out by positioning, preferably transpylorically, one end of the enteral tube at a site of inflammation in the lower G.I. tract and connecting the other end to a source of 5-ASA or other comparably topically active compound.

The tube may be introduced into the body by a number of means e.g. nasally, orally or abdominally via a naso/oral directed gastrostomy, as shown, for instance, in the abovementioned July 1987 Ross catalogue.

Positioning of the bolus end of the tube in the desired location may be achieved using a endoscope in optional conjunction with radioopacity in the tube for later X-ray confirmation of correct positioning.

A selected amount of the solution or suspension containing the active compound is expelled from the implanted bolus of the tube using an irrigation syringe, a Luer syringe or other kind of fluid injection device (e.g. plastic bottle) insertable into the end of the tube outside the body.

The effective dose depends on the extent of the disease and for adults it is usually in the range from 2 to 5.6 g per day (24 hrs). The preferred range is from 3 to 4.5 g per day.

Where the active compound is ASA, up to 80 mg/kg body weight of 5-ASA, 4-ASA or 3-ASA will be the recommended initial daily dosage subject to adjustment in accordance with the observed results of treatment. In particular the dosage for children should be adjusted following measurements of serum concentration, and of renal and hepatic functions.

The most preferred dosage is 4g of 5-ASA per day. This is preferably delivered gradually throughout the day of treatment in a volume of up to 240 ml of the suspension mentioned above. Administration over the longest period possible during the day of treatment is preferred as this minimizes absorption and maximizes topical effectiveness.

Treatment should be by instillment of 1 dosage unit (as above) per day for 2 months or longer. Two half dosage units may be instilled daily as an alternative to diminish peak absorption level of 5-ASA or N-acetyl-5-ASA.

In the following trials, the suspension given in table 1 was used in a dosage unit of 4g per day of 5-ASA per 240 ml of suspension.

TABLE 1

| AMOUNT per UNIT | | | |
|---|---|---|---|
| Label per 60 g | Actual % w/w | INGREDIENTS | BATCH AMOUNT |
| | 85.0 | Water RODI | 170,000 g |
| | 0.10 | Sodium Benzoate | 200 g |
| | 0.075 | Carbopol 934P | 150 g |
| | 0.10 | Disodium EDTA | 200 g |
| | 0.468 | Potassium Metabisulfite | 936 g |
| | 0.41 | Potassium Acetate | 820 g |
| | 0.25 | Xanthan Gum | 500 g |
| 1.0 g | 1.7 | 5-Aminosalicylic Acid | 3.400 g |
| | to complete | Water RODI | 20,000 g |
| | | Water RODI QS to | 200.000 g |

In three patients subjected to this therapy, the following results were reported:

1. a 32-year old female with no active ileal disease (had small ileectomy five years ago) experienced no side effects.

2. a 66-year old female with active small bowel Crohn's disease, from the duodenum to the ileum, started to improve in the third week of a 4g/day treatment regimen; bowel movements were down to 3/4 per day, no pain was experienced and the inflammatory indices improved. The patient had a total of 4 weeks of the 4g/day regimen followed by enteral feeding. She thus gained 15 pounds in weight and was discharged much improved with 3 formed bowel movements per day as compared to 15-18 per day on admission. 3. a 56-year old female with 3 inflammatory strictures in her small bowel, and having had a previous ileocolic resection, started to improve after 2 weeks of a 4 g 5-ASA/-day regimen. On the 21st day of therapy she had gained 5 pounds in weight and was symptom-free. This patient was also on prednisone and enteral feeding.

These studies are impressive, demonstrating a clear clinical response in severe proximal Crohn's disease and a consequent avoidance of the need for further surgery. No clinical side effects were noted and renal function and hematology were unchanged. No new abnormalities developed in these patients.

The augmented availability of 5-ASA achieved through treatment by the method according to the invention is demonstrated by impressive clinical results showing that the 5-ASA is in topical contact with the inflamed portion of the bowel. Excessive absorption is avoided as it would limit the prolonged treatment of inflammation by direct contact.

The following results profile the characteristics of both short-term (single) and steady state administration of 5-ASA or like compounds to the small bowel as determined by plasma concentrations of 5-ASA and of the only major metabolite of 5-ASA identified in man, viz: N-acetyl-5-aminosalicYlic acid. Following the method of the present invention, both free and acetylated forms can be found in plasma within 1 to 2 hours post administration.

Plasma levels are negligible approximately 12 hours after dosing as shown in table 2. The absorption peak is in the range from 4 to 8 hours after treatment. Notably, absorption of 5-ASA into the blood is greater when compared to an equivalent dose administered rectally.

TABLE 2

| | concentration in plasma in mcg/ml of | | | | | | | |
|---|---|---|---|---|---|---|---|---|
| | Patient SJM 1 | | Patient NF 2 | | Patient JAT 3 | | Patient CSD 4 | |
| hours after 1 dose | 5-ASA | N-Ac 5-ASA | 5-ASA | N-Ac | 5-ASA | N-Ac | 5-ASA | N-Ac |
| 0 | 0.032 | 0.056 | 0 | 0.747 | 0.012 | 0.01 | 0.099 | 0.253 |
| 1 | 4.87 | 8.01 | 15.7 | 15.2 | 8.9 | 12.9 | 11.1 | 11.6 |
| 2 | 11 | 22.6 | 15.5 | 17.9 | 15.9 | 20.7 | 17.1 | 19.7 |
| 3 | 10.4 | 18.7 | 17.2 | 21.5 | 11.1 | 18.9 | 12.6 | 20.2 |
| 4 | 19.2 | 28.8 | 16.8 | 21.4 | 10.2 | 20.8 | 9.29 | 16.4 |
| 5 | 5.8 | 15.9 | 6.46 | 13.8 | 5.71 | 18.1 | 4.8 | 12.6 |
| 6 | 2.2 | 10.4 | 2.7 | 10 | 2.83 | 10.9 | 2.74 | 8.23 |
| 7 | 0.921 | 5.3 | 1.43 | 5.49 | 1.34 | 6.48 | 1.27 | 4.51 |
| 8 | 0.811 | 4.41 | 0.55 | 4.24 | 0.813 | 6.02 | 0.263 | 3.53 |
| 8½ | — | — | — | — | — | — | — | — |
| 12 | 0.02 | 0.506 | 0.119 | 2.22 | 0.085 | 1.2 | 0 | 0.947 |
| 24 | — | — | — | — | — | — | — | — |

| | concentration in plasma in mcg/ml of | | | | Healthy Volunteers (n = 6) average | | |
|---|---|---|---|---|---|---|---|
| | Patient JS 5 | | Patient ML 6 | | | | |
| hours after 1 dose | 5-ASA | N-Ac 5-ASA | 5-ASA | N-Ac 5-ASA | hours after 1 dose | 5-ASA | N-Ac 5-ASA |
| 0 | 0.328 | 0.031 | 0 | 0.038 | 0 | 0.118 | 0.189 |
| 1 | 10.3 | 13.5 | 6.55 | 9.32 | 1 | 9.57 | 11.75 |
| 2 | 15.2 | 23.5 | 8.49 | 14.9 | 2 | 13.86 | 19.88 |
| 3 | 25.4 | 35.9 | 10.1 | 22.3 | 3 | 14.46 | 22.92 |
| 4 | 15.7 | 28.1 | 9.39 | 20.8 | 4 | 13.43 | 22.72 |
| 5 | 6.17 | 19.4 | 7.85 | 22 | 5 | 6.01 | 16.97 |
| 6 | 2.12 | 11 | — | — | 6 | 2.52 | 10.11 |
| 7 | 1.15 | 6.63 | — | — | 7 | 1.22 | 5.68 |
| 8 | 0.473 | 4.22 | 0.34 | 6.21 | 8 | 0542 | 4.772 |
| 8½ | — | — | — | — | — | — | — |
| 12 | 0.052 | 0.811 | 0.577 | 1.83 | 11.5 | 0.142 | 1.25 |
| 24 | — | — | — | — | | | |

The concentrations in blood appear to be slightly higher and reached sooner in healthy volunteers as compared to Crohn's patients (table 3.). This phenomenon may be explained by the fact that Crohn's patients absorb lesser quantities of 5-ASA.

TABLE 3

| | 5-ASA (time) mcg/ml | N-Ac 5-ASA (time) mcg/ml |
|---|---|---|
| Patients | 10.96 (4 h) | 23.37 (6 h) |
| Volunteers | 14.46 (3 h) | 22.96 (3 h) |
| difference | +3.5 mcg/ml (+31.9%) | −0.41 (−1.7%) |

As shown in Table 4, urinary excretion accounts for about ⅓ the dose. 24 hour urinary analysis of patients undergoing treatment according to the invention reveals safe levels of both 5-ASA and N-acetyl 5-ASA throughout treatment. This confirms useful but not excessive availability of 5-ASA in the duodenum, jejunum, small bowel and subsequent segment, of the lower G.I. tract.

TABLE 4 urinary excretion after 24 hours post-treatment amounts excreted in mg's

| | amount excreted | |
|---|---|---|
| | 5-ASA | N-Ac 5-ASA |
| Volunteers | | |
| JAT | 832.5 | 1738 |
| SJM | 995.8 | 1952.9 |
| CSD | 90.6 | 634.2 |
| JWS | 1163.4 | 1791.2 |
| NRF | 1460.2 | 2300.8 |
| average | 908.5 | 1683.4 |
| Patients | | |
| EP | 747.5 | 1563.8 |
| LB | 306.9 | 1494.5 |
| YAF | 370.9 | 1535.4 |
| MD | 214.65 | 1459.8 |
| WS | 1109.6 | 269.8 |
| average | 549.9 | 1750.3 |

The urinary excretion appears slightly higher in volunteers (64.7%) as compared to patients (53.6%).

As noted above, overabsorption of 5-ASA is undesirable since it may be necessary for (for example jejunally instilled 5-ASA solution to retain some of its active ingredient by the time it reaches the colon. This would ensure that more distal areas of inflammation can successfully be treated by installation of 5-ASA solution in the proximal small bowel eg in cases of fulminant ulcerative colitis.

The treatment represented in this invention achieves this delivery profile as confirmed by analysis of 5-ASA and N-Ac-5-ASA in stools passed by patients undergoing treatment shown in table 5.

In analyses of faeces excreted on a given day after treatment initiation (1 dosage unit =4g of 5-ASA in 240 ml of suspension day) the following results (table 5) were obtained:

TABLE 5 fecal excretion after 9 hours post-treatment amount excreted in mg's

| | amount excreted | |
|---|---|---|
| | 5-ASA | N-Ac 5-ASA |
| Volunteers | | |
| JAT | 36.8 | 242.75 |
| SJM | 13.2 | 92 |
| CSD | 11.1 | 60.4 |
| JWS | 16.9 | 498.5 |
| NRF | 1.9 | 5 |
| ML | 16.5 | 28.5 |
| average | 16.06 | 154.7 |
| Patients | | |
| EP | 7.4 | 23.51 |
| LB | 400.7 | 53.6 |
| YAF | 1.2 | 119.6 |
| EM | 28.7 | 6.09 |
| MD | 23.8 | 495.3 |
| WS | 28.6 | 476.3 |
| average | 81.7 | 195.8 |

These results sow that both the active ingredient (5-ASA) and its metalolite (N-acetyl 5-ASA) are available for therepeutic effect at the distal limit of the G.I. tract (anus). Also, the amounts found on the faeces of patients is higher than in volunteers (6.9% vs 4.2%), thus confirming a lower absorption in patients and illustrating availability of the tropically active ingredient to excert a topical antiphlogestic or lower gastrointestinal anti-inflammatory action on sites of inflammations along the lower G.I. track.

Serum levels furthermore demonstrate that 5-ASA is available in the serum should a systemic role be demonstrated. Furthermore, the fact that urinary clearance is not excessive and that a degree of fecal recovery occurs, shows that the method according to the invention may be used to deliver free 5-ASA to the entire lower G.I. tract beyond the point of administration.

CONTRAINDICATIONS FOR 5-ASA

Active peptic ulcer (possibly).
Hypersensitivity to salicylates.
Infants under 2 years of age.
Urinary tract obstructions.

WARNINGS 5-aminosalicylic acid should be used only after critical appraisal of the risk to benefit ratio in the following situations:
Liver and kidney disease.
Bleeding and clotting disorders.
Pregnancy and lactation

PRECAUTIONS

Periodic urinalysis to assess kidney function is recommended since prolonged 5-aminosalicylic acid therapy may damage the kidneys (see toxicology). Caution should be exercised when 5-aminosalicylic acid is first used in patients known to be allergic to sulfasalazine. The patients should be instructed to discontinue therapy at the first sign of rash or fever.

Drug interactions. No known drug interactions exist. The hypoglycemic effect of sylfonylureas may be enhanced. Interactions with coumarins, methotrexate, probenecid, sulfapyrazone, spironolactone, furosemide and rifampicine can not be excluded. Potentiation of undesirable glucocorticoid effects on the stomach is possible.

ADVERSE REACTIONS

Adverse reactions linked to the sulfapyridine moiety of sulfasalazine are avoided with the present invention. Hypersensitivity reactions have been reported in a subgroup of patients known to be allergic to sulfasalazine including rash, fever, and dizziness. The apparent frequency is estimated at 3–4% (15-51), with reactions occuring at the onset of therapy and resolving promptly following discontinuance.

In rare cases, following oral 5-ASA administration, exacerbation of ulcerative colitis characterized by cramping, acute abdominal pain and diarrhea has been reported. Acute pancreatitis, pericarditis, hepatitis, and pleural effusion have also been reported in association both with oral 5-ASA and SAS.

Other reported side effects include headache, flatulence, nausea, and alopecia, but do not appear to be common.

DOSAGE AND ADMINISTRATION

The suspension (4g 5-ASA per 240 ml) is administered on a daily basis during acute episodes of disease and at other times during the usual course of therapy is again one unit daily. Response to treatment and adjustment in dosing frequency should be determined by periodic examination, including endoscopy and the assessment of symptomatology including rectal bleeding, stool frequency, and general well-being.

Daily dosing is continued until a significant response is achieved or the patient achieves remission. Usually the dose can be reduced to alternate days or every third day, depending upon disease activity. Abrupt discontinuance of 5-ASA is not recommended. Dose tapering is recommended and serum levels in each patient should be titrated to meet individual needs. Maintenance therapy is recommended to assure continued remission. The dosing schedule, alternate day, every third day, or p.r.n. should be determined for each patient. If symptoms, diarrhea and rectal bleeding recur, dosage should be increased to the previous effective level.

In children between the ages of 2 and 12, use of the drug should be limited to situations where a clear benefit is expected.

PHARMACOLOGY

5-ASA is also known as 5-aminosalicylic acid, mesalamine (USAN), mesalazine, 5-amino-2-hydroxybenzoic acid or 5-ASA:. It has empirical formula $C_7H_7NO_3$ and a Mol. Wt. of 153.14.

The following is a comprehensive presentation of the results of pharmacologic tests conducted on 5-ASA.

In tests using the oral route of administration (mostly 500 mg/kg), no adverse effect of 5-ASA on the following parameters or in the following tests could be established: tremorine antagonism, hexobarbital sleep time, motor activity, anticonvulsant action (metrazol & electric shock), blood pressure, heart rate, respiratory rate (up to 10 mg/kg, i.v.), tocolysis (antispasmodic assay), local anaesthesia, antihyperthermal and antipyretic effects. In the paw-edema test with carrageen injection, 200 mg/kg per os proved ineffective, but 500 mg/kg 5-ASA per os exhibited mild antiphlogistic action. In the renal function tests (natriuresis and diuresis) no biologically relevant effects of 200 mg/kg per os were demonstrated. After 600 mg/kg, marked functional changes were observed: increases in both total urinary output, natriuresis and proteinuria. The urinary sediment contained increased numbers of erythrocytes and epithelial cells. Both potassium elimination and specific weight were reduced. It can be concluded from these experiments that even high doses of 5-ASA have no effect on vital parameters. Disturbances in renal function are to be expected only at dosages equivalent to a single dose at least 8 to 10 times the daily dose in man.

TOXICOLOGY

A full battery of animal toxicology studies including long-term carcinogenicity and toxicity studies provide a plethora of safety data. Hereinafter there is a list of these studies and report summaries of the 13-week and 6-month studies on rat and dogs respectively as well as a discussion of the nephrotoxic potential of 5-ASA.

List of 5-ASA Animal Toxicology Studies

1. ACUTE TOXICITY
Oral LD50 —Rats and Mice
IV LD50 —Rats and Mice
2. SUB-CHRONIC TOXICITY
4 and 13 week oral —Rats/(0, 40, 160 & 640 mg/kg/day)
3. CHRONIC TOXICITY
6-Month Oral —Dogs/(0, 40, 80 & 120 mg/kg/day)
18-Month Oral CA/toxicity —Mice
24-Month Oral CA only —Rats
4. LOCAL/MUCOSAL
(for Rectal Dosage Forms)
Primary eye irritation —Rabbits
Rectal Tolerability —Rabbits
Delayed Contact Sensitization —Guinea Pig
Rectal Mucosal Irritation —Dog
5. REPRODUCTION AND EFFECTS ON FETUS
Oral Embryotoxicity and Teratogenicity
Rats: 0, 80, 160, 320 mg/kg/day
Rabbits: 0, 55, 165, 496 mg/kg/day
Fertility, Segment I—Rats
Week Male Fertility—Rats
6. CARCINOGENICITY
Mutagenicity
Microsome Mutation Assay/*Escherichia Coli*
Mouse Micronucleus Assay
In vivo Sister Chromatid Exchange
Assay, Hamster Bone Marrow Cells
Fluctuation Test/Klebsiella
pneumoniae and Ames Test/
*Salmonella typhrimurium*
Carcinogenicity—see 3.b above Brief summary of findings to date: Animal studies to date show the kidney to be the only significant target organ for 5-ASA toxicity in rats and dogs. At high doses, the lesions consisted of papillary necrosis and multifocal proximal tubular injury. In rats, the "no-effect" levels were 160 mg/Lg/day for females and 40 mg/kg/day for males (minimal and reversible tubular lesions seen) after 13 weeks of oral administration. In dogs, the "no effect" level in both males and females was 40 mg/kg/day after six months oral administration. Aside from gastric and heart lesions, bone marrow depression, (seen in some of the rats at the 640 mg/kg/level,) and, secondary effects of the kidney damage previously considered, no other sign of systemic toxicity was noted at daily doses up to 160 mg/kg in rats and 120 mg/kg in dogs for 13 week and six month periods, respectively.

Mucosal irritation studies in rabbits (5 day) and dogs (27 day) with rectally administered 5-ASA dosage forms indicated that 5-ASA was devoid of significant local irritation on rectal mucosa both macroscopically and microscopically.

The battery of tests completed shows that 5-ASA is devoid of embryotoxicity and teratogenicity in rats and rabbits; that it does not affect male rat fertility after 5 weeks oral administration at 296/mg/kg/day; that it lacks the potential to affect late pregnancy, delivery, lactation or pup development in rats; and that it is without mutagenic properties in a standard series of tests.

Nephrotoxic potential of 5-Aminosalicylic Acid.

Owing to its structural relationship both to phenacetin, the aminophenols and salicylates, 5-ASA was included in a series of compounds studied following identification of antipyretic-analgesic nephropathy in humans. Calder et al. (Brit. Med. J., 27 Nov. 1971; Brit. Med. J., 15 Jan. 1972; Xenobiot Vol. 5, 1975) reported that in rats in addition to the proximal tubule necrosis seen with aspirin and phenacetin derivatives, 5-ASA produced papillary necrosis following single intravenous doses ranging from 150 mg/kg to 872 mg/kg.

Diener et al (Archives of Pharm. 1986: 326:278-282) have shown that oral daily doses of 30 mg/kg and 200 mg/kg of 5-ASA for four weeks failed to produce any adverse effects on kidney function or histology in the rat.

In a 13-week study on rats, no renal lesion was detected after 4 weeks in the animals receiving up to 160 mg/kg orally per day. However, severe papillary necrosis and proximal tubular injury was seen in most animals receiving 640 mg/kg orally per day. At 13 weeks, the female animals were free of pathology with doses up to 160 mg/kg; minimal and reversible lesions in the tubules occurred in a few males (with no changes in renal function) at the 40 mg/kg level.

After six months oral administration in dogs, no toxicity was seen in the 40 mg/kg/day group. At 80 mg/kg/day, 2 of 8 treated showed slight to moderate renal papillary necrosis. These dogs as well as 2 others showed minimal to moderate tubular lesions. At 120 mg/kg/day, 2 females had slight papillary necrosis. These and 2 others showed minimal to moderate tubule injury.

Thus, the animal toxicity data suggest that 5-ASA has a nephrotoxic potential comparable to aspirin; on the other hand, extensive investigations of the problem of analgesic nephropathy have led to a current consensus that it is the combination of products that provides the greatest hazard, and that single ingredient antipyretic-analgesics such as aspirin are safe when taken in reasonable doses. See Emkey (Amer. J, Med., 24 June 1983) and Editorial (Amer. Pharm., May 1984).

It is important to note that despite 40 years' use of sulfasalazine world-wide for treatment and long-term prophylaxis of ulcerative colitis and Crohn's disease, there has been no report of kidney disease directly attributable to the drug or to the diseases being treated. The fact that sulfasalazine resulting in therapeutic levels of sulfapyridine might have led to kidney disease is taken as a systemic complication of inflammatory bowel disease, but applicants' are aware of no report listing kidney disease as a complication either of ulcerative colitis or of Crohn's disease.

While there have been shown and described what are at present believed to be the preferred embodiments of the invention, it will be obvious to those skilled in the art that various changes and modifications may be made to them without departing from the scope of the invention as defined by the appended claims.

The embodiments of the invention in which an exclusive property or privilege is claimed are defined as follows:

1. A method of delivery of an effective amount of an anti-inflammatory agent directly to the lower gastrointestinal tract in patients suffering from inflammatory bowel disease comprising:
   (a) providing a pharmaceutically acceptable solution including said anti-inflammatory agent;
   (b) providing an enteric tube having first and second ends;
   (c) inserting the first end of the enteric tube into the lower gastrointestinal tract distal to the stomach of a patient to be treated; and
   (d) introducing said solution into the second end of said tube to expel a desired amount of said solution from said first end into said tract;
whereby said agent is brought into direct, topical contact with inflamed parts of the tract, while avoiding prior degradation in the stomach.

2. A method according to claim 1, wherein said agent is selected from the group consisting of 5-ASA, 4-ASA and 3-ASA.

3. A method according to claim 2, wherein said inserting step is done transpylorically.

4. A method according to claim 3, wherein said inserting step is done orally or nasally.

5. A method according to claim 3, wherein said inserting step is done by gastrostomy.

6. A method according to claim 2, wherein said agent is 5-ASA and is dosed in amount ranging from 2 to 5.6g of 5-ASA daily.

7. A method according to claim 2, wherein said agent is 5-ASA and is dosed in amount ranging from 3 to 4.5 g of 5-ASA daily.

* * * * *